(12) United States Patent
Vanella (10) Patent No.: US 9,643,192 B2
(45) Date of Patent: May 9, 2017

(54) FILTERING ASSEMBLY AND FILTERING METHOD FOR AIR AND GASEOUS FLUIDS IN GENERAL

(71) Applicant: TECNOLOGICA S.A.S. DI VANELLA SALVATORE & C., Pesaro (IT)

(72) Inventor: Salvatore Vanella, Monteciccardo (IT)

(73) Assignee: TECNOLOGICA S.A.S. DI VANELLA SALVATORE & C., Pesaro (IT)

(*) Notice: Subject to any disclaimer, the term of this patent is extended or adjusted under 35 U.S.C. 154(b) by 267 days.

(21) Appl. No.: 14/275,052

(22) Filed: May 12, 2014

(65) Prior Publication Data

US 2014/0377136 A1 Dec. 25, 2014

(30) Foreign Application Priority Data

Jun. 19, 2013 (IT) ................ BO2013A0308

(51) Int. Cl.
*B03C 3/12* (2006.01)
*A61L 9/16* (2006.01)
(Continued)

(52) U.S. Cl.
CPC ....... *B03C 3/12* (2013.01); *A61L 9/00* (2013.01); *A61L 9/16* (2013.01); *A61L 9/22* (2013.01);
(Continued)

(58) Field of Classification Search
CPC .............. A61L 9/00; B03C 3/12; B03C 3/155
(Continued)

(56) References Cited

U.S. PATENT DOCUMENTS

| 5,807,425 A | 9/1998 | Gibbs |
| 7,473,304 B2* | 1/2009 | Besi ............. B01D 46/50 422/121 |

(Continued)

FOREIGN PATENT DOCUMENTS

| EP | 0644379 A1 * | 9/1993 |
| JP | 2003279089 A | 10/2003 |
| JP | 2003308947 A | 10/2003 |

OTHER PUBLICATIONS

European Search Report for EP 14 16 7861 dated Sep. 26, 2014, (3 pages).

*Primary Examiner* — Sean E Conley
(74) *Attorney, Agent, or Firm* — Abelman, Frayne & Schwab (57) ABSTRACT

A filtering assembly for air and gaseous fluids in general is provided comprising a duct, which can be crossed by a gaseous fluid carrying pollutants. The filtering assembly comprises: at least one filtering station to remove toxic gases and solid particle pollutants of dimensions preferably greater than 50 μm; at least one conductive grille, having at least one hole which faces and is proximate to at least one conductive filament being kept at a negative electric potential for the emission of electrons, which can be paired with pollutants of the solid particles and micro-organisms type of dimensions preferably between 10 nm and 50 μm, at least one accumulation plate downstream of the grille, maintained at a positive electrical potential for the stable collection of pollutants paired with the electrons at least one emission source of ions, for the restoration of electric charge of the gaseous fluid, flowing over the source.

27 Claims, 3 Drawing Sheets

(51) Int. Cl.
*A61L 9/22* (2006.01)
*B03C 3/41* (2006.01)
*F24F 3/16* (2006.01)
*A61L 9/00* (2006.01)
*B03C 3/155* (2006.01)
*B03C 3/08* (2006.01)
*B03C 3/09* (2006.01)
*B03C 3/36* (2006.01)
*B03C 3/47* (2006.01)
*H01T 23/00* (2006.01)
*A61L 2/10* (2006.01)

(52) U.S. Cl.
CPC .................. *B03C 3/08* (2013.01); *B03C 3/09* (2013.01); *B03C 3/155* (2013.01); *B03C 3/368* (2013.01); *B03C 3/41* (2013.01); *B03C 3/47* (2013.01); *F24F 3/166* (2013.01); *A61L 2/10* (2013.01); *A61L 2209/14* (2013.01); *B03C 2201/10* (2013.01); *F24F 2003/1614* (2013.01); *F24F 2003/1625* (2013.01); *F24F 2003/1628* (2013.01); *F24F 2003/1667* (2013.01); *F24F 2003/1682* (2013.01); *H01T 23/00* (2013.01)

(58) Field of Classification Search
USPC .................................. 422/122; 95/69; 96/55
See application file for complete search history.

(56) References Cited

U.S. PATENT DOCUMENTS

| | | | |
|---|---|---|---|
| 7,976,616 B2 * | 7/2011 | Alam | B03C 3/41 313/351 |
| 2003/0221999 A1 | 12/2003 | Weaver et al. | |
| 2011/0102963 A1 | 5/2011 | Sekoguchi | |

* cited by examiner

FILTERING ASSEMBLY AND FILTERING METHOD FOR AIR AND GASEOUS FLUIDS IN GENERAL

TECHNICAL FIELD

This invention relates to a filtering assembly and a filtering method for air and gaseous fluids in general.

BACKGROUND ART

As known, the attention to the conditions of health and hygiene in closed environments in which individuals operate is always higher, both for those buildings (hospitals, clinics, nursing homes, healthcare homes, and the like) where absolute lack of pollutants, pathogens, microbes, etc., is an essential obligation by the very nature of the activities that take place in these buildings, and, more in general, for any place, whether public or private, in which one or more people are likely to stay for longer or shorter periods.

Furthermore, it is appropriate to observe that in the air that is breathed inside closed environments, various types of pollutants and/or potentially dangerous to humans are contained. In addition to dust and particles of varying size (from a dimension of a few microns up to nanometers), it is in fact possible, for example, to find in the air toxic gases or micro-organisms of various nature (viruses, bacteria, spores, moulds, fungi, etc.). Furthermore, sometimes a lack of negative ions is detected, which de facto determines a sort of "electrical" pollution, which has to be counteracted to ensure the optimal conditions of hygiene and healthiness.

The precautions or the remedies that are normally adopted usually consist of selective action filters, directed, that is to say, towards a specific category of undesirable substance (and often, as in the case of anti-particulate filters, they prove to be ineffective against particles of finer dimensions).

Therefore, it appears evident how it is difficult, if not impossible, to ensure filtering, and the elimination of all the different types of polluting substances, as vice versa required by the increasingly stringent hygienic/sanitary requirements, unless resorting to complex infrastructures and plants of difficult installation which, due to high costs and/or to logistical problems, often prove uneconomic (and therefore unusable) for most of the applications.

SUMMARY

Main purpose of this invention is to solve the problems described above by providing an air filtering assembly, and gaseous fluids in general, which proves to be effective against different types of pollutants.

Within this aim, an object of the invention is to propose a method which allows an air filtering and gaseous fluids in general, against different types of pollutants.

Another object of the invention is to provide a filtering assembly that ensures health and well-being, to individuals who operate in environments in which it is installed.

Still another object of the invention is to provide an assembly that ensures an effective filtering, without requiring significant periodic maintenance interventions.

A further object of the invention is to provide an assembly that ensures an effective air filtering, against particulates of any size, of micro-organisms, toxic gases, by rebalancing simultaneously the content of negative ions.

A further object of the invention is to provide an assembly of secure implementation and which ensures high reliability of operation.

Last but not least, object of the invention is to provide a low cost assembly, and which can be easily obtainable starting from elements and materials commonly available commercially.

Still another object of the invention is to propose a method that is workable in a simple way and with contained costs.

This task and these objects are achieved by a filtering assembly for air and gaseous fluids in general, comprising a duct, crossed by a gaseous fluid, carrying pollutants of various types, characterised in that it comprises: at least one filtering station, for the removal of pollutants of the toxic gases and solid particles type of dimensions preferably greater than 50 μm; at least one conductive grille, having at least one hole that faces and that is proximate to at least one conductive filament, said at least one grille and said at least one filament being kept at a negative electrical potential, for the emission of electrons, which can be paired with pollutants such as solid particles and micro-organisms, preferably having dimensions between 10 nm and 50 μm, downstream of said grille there being at least one accumulation plate, which is kept at a positive electric potential, for the stable collection of pollutants paired with the electrons; at least one source of emission of ions, for the restoration of the electric charge of the gaseous fluid, flowing over said source.

This task and these objects are also achieved by a method of filtering for air and gaseous fluids in general, which consists in: affecting a gaseous fluid which carries pollutants of various types, with a flow of electrons, emitted by at least one conductive grille, which is arranged along said duct and has at least one hole, and by at least one conductive filament, which faces and is proximate to said at least one hole, said grille and said at least one filament being kept at a negative electric potential, for pairing of the electrons with pollutants of the type of solid particles and micro-organisms, with dimensions preferably between 10 nm and 50 μm; stably collect the pollutants paired with the electrons, on at least one accumulation plate, kept at a positive electrical potential, which is arranged along said duct downstream of said at least one grille; restoring the electric charge of the gaseous fluid, by at least one emission source of ions, arranged along said duct downstream of said grille and of said at least one accumulation plate, removing from the gaseous fluid, in a preventive phase or subsequent or intermediate to the previous said phases, pollutants of the type of toxic gases and solid particles with dimensions preferably greater than 50 μm at at least one filtering station, arranged along a duct, that can be crossed by the gaseous fluid.

BRIEF DESCRIPTION OF THE DRAWINGS

Further characteristics and advantages of the invention will become apparent from the description of two preferred embodiments, but not exclusive, of the assembly (and the method) according to the invention, illustrated by way of non-limitative example in the accompanying drawings, in which.

DESCRIPTION OF PREFERRED EMBODIMENTS OF THE INVENTION

With particular reference to the cited Figures, it is generally indicated by reference number 1 an assembly responsible for the filtering of air and more in general of any gaseous fluid, carrying pollutants of various types (as will be better explained in the following pages).

It is specified as from now that, according to the preferred embodiment, the treated gaseous fluid is air and therefore, reference will be made to it here below in the present description. In fact, in this preferred embodiment, assembly 1 can be placed at a piping of any air-conditioning, airing, ventilation, heating, etc., plant to thus be able to perform filtering and depollution of the air that flows through the piping, before it is emitted in a closed environment (hospitals, clinics, nursing homes, healthcare homes, and the like, but also workplaces, public buildings, private buildings, housing, etc.). On the other hand, assembly 1 can be simply arranged in proximity to the involved environment, to take polluted air from the latter and return it after filtering treatment.

It is not excluded, moreover, the use (anyhow falling within the protection scope claimed herein) of assembly 1 for the filtering of different gaseous fluids, depending on the specific needs.

For example, assembly 1 can be used effectively along an output circuit of the exhaust gas, smoke, and the like, before their release into the external environment.

In each case, assembly 1 comprises a duct 2, which can be crossed by the gaseous fluid and which, for example, is defined by a shaped shell 3 (placeable along the piping leading into the closed environment or along the output circuit mentioned above).

According to the invention, the assembly 1 comprises: at least one filtering station, at least one conductive grille 4, having at least one hole 5 which faces and is proximate to at least one conductive filament 6, at least one accumulation plate 7, located downstream of grille 4 and at least one emission source of ions A (negative, in the preferred embodiment described herein, by way of non limiting purpose), to restore the electric charge which is desired to give to the gaseous fluid, flowing over the source thereof, before its output from the duct 2 (at the end of the filtering treatment).

Figure 1:
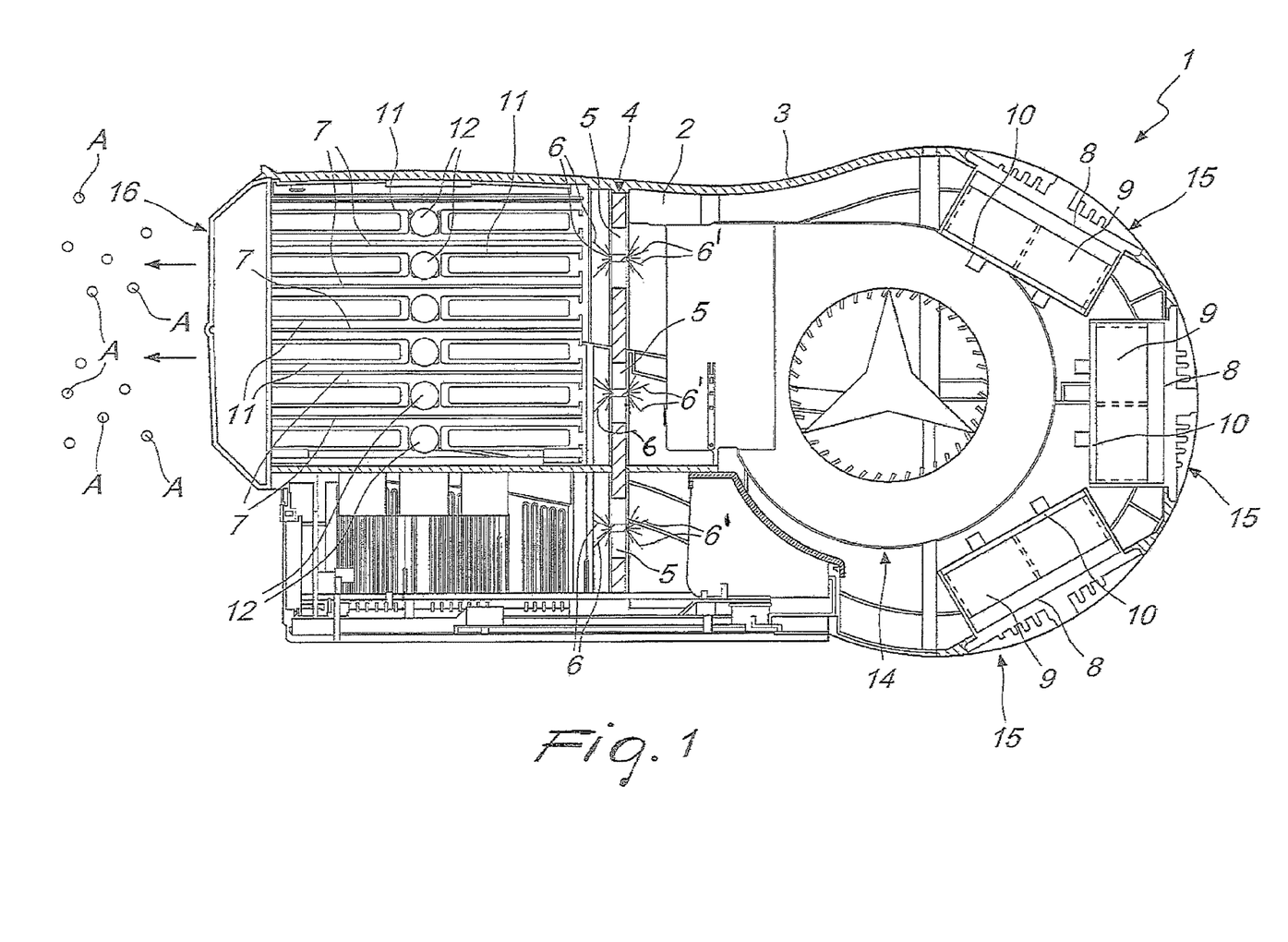
FIG. 1 illustrates schematically the filtering assembly according to the invention, in side elevation and partially sectioned.

It must be noted how, in the preferred embodiment, the above introduced elements (the station, the grille 4 and the accumulation plate 7, the emission source), are arranged in series along the duct 2 in the same sequence in which they were listed in the previous paragraph (and in which are shown in FIG. 1), but it is not excluded the possibility to provide assemblies 1 in which these elements are differently ordered and placed, without thereby departing from the scope of protection claimed herein.

Through the filtering station, it is thus possible to remove (as will be better illustrated in the following pages) pollutants of the type of toxic gases and solid particles having sizes preferably greater than 50 μm.

Furthermore, the grille 4 and the filament 6 are kept at a negative electric potential (the value of which, also variable in time and also different between the grille 4 and the filament 6, can be selected at will, depending on the specific needs), in such a way as to emit electrons into the surrounding environment, which can thus be paired (for example, by electrostatic attraction), with pollutants of the type of solid particles and micro-organisms, having dimensions preferably between 10 nm and 50 μm, carried by air.

More precisely, in fact, the conductive filament 6 constitutes a preferred emission source of electrons, which results to be arranged at the passage area of at least a part of the air (which in fact crosses the hole 5), in such a way as to ensure an optimal pairing with a very high number of pollutants to which the filament 6 thereof is responsible for.

A negative electrical charge is thus attributed to such pollutants, to force the stable collection by means of the accumulation plate 7, for this purpose kept at a positive electrical potential and arranged downstream of the grille 4.

It must be noted how the accumulation plate 7 can be easily removed, periodically, for a possible maintenance.

It is also specified that there is the possibility of equipping the assembly 1 of a number at will of accumulation plates 7, arranged in the duct 2 according to various configurations (even two by two facing, with interposition of insulating material layers), depending on the specific needs: for example, in the accompanying Figures are proposed embodiments, which envisage resorting to the use of accumulation plates 7 arranged in parallel along the duct 2.

It is specified that there is the possibility that assembly 1 comprises at least a first conductive filament 6, kept at a negative electric potential, which faces and is approximate to the hole 5 and arranged downstream of the grille 4, and at least a second conductive filament 6', kept at a negative electric potential, which faces and is approximate to the opening 8 and arranged upstream of the grille 4. Thus they fall within the scope of protection hereby claimed, embodiment solutions in which at least one filament 6 is arranged only downstream (or only upstream) of the grille 4, as how embodiment solutions (preferred) in which at least one filament 6' is arranged upstream and at least one filament 6 is arranged downstream thereto.

Figure 2:
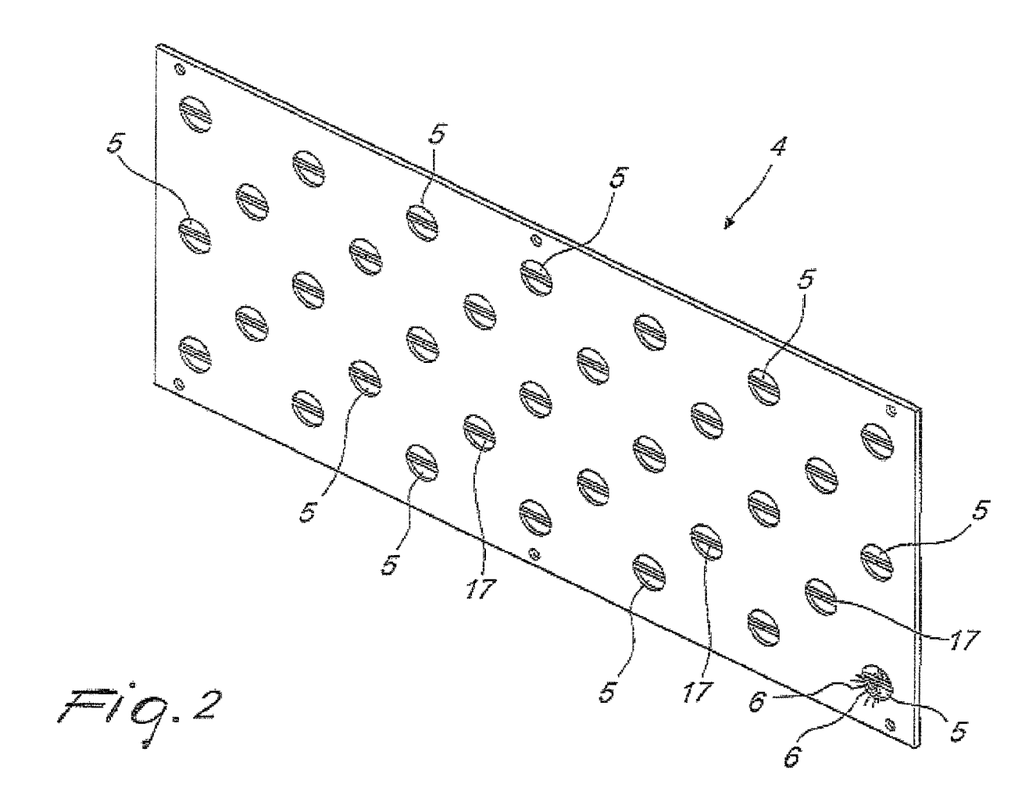
FIG. 2 schematically illustrates the conductive grille, in perspective view, in the first embodiment.

Obviously, the possibility that the grille 4 includes a plurality of holes 5, with a respective conductive filament 6 facing each one of them, is not excluded. More particularly, in the preferred embodiment, given in the attached Figures by way of illustrative and non-limiting application of the invention, the conductive grille 4 has a plurality of holes 5, and each one of them faces and is proximate to a respective plurality of conductive filaments 6,6', some of which are arranged downstream of each hole 5, others being arranged upstream of each hole 5 (as can be seen in FIG. 1, while in FIG. 2, for simplicity, filaments 6 approximate to a single hole 5 are represented).

In this way, the entire mass of air that runs through the duct 2 is forced to cross the grille 4 at one of the holes 5 thereof, therefore flowing over filaments 6,6' which emit in the immediate proximity a very high number of electrons: the assembly 1, according to the invention, thus ensures great effectiveness since the air is forced to run through the area in which emission of electrons is maximum, thus ensuring the pairing of the latter with a very high number of pollutants consisting of solid particles (having the sizes as mentioned above).

Usefully, the aforementioned filtering station may comprise: at least one perforated plate 8, which in its turn comprises at least one opening, having dimensions preferably between 150 μm and 250 μm (for example 200 μm), at least one active carbon filter 9 and at least one electrically polarised fibre filter 10.

In this way, above all, the air enters the shell 3 and in the duct 2, passing freely through the opening of perforated plate 8, which vice versa selectively locks the pollutants of the solid particles type having larger dimensions than those of the opening.

Subsequently, the action of the active carbon filter 9 allows adsorbing pollutants of toxic gases type present in the environment, from which comes the air treated with the assembly 1.

To this purpose, it is specified that it is envisaged the possibility to add suitable additives, in compositions designed specially, to make the active carbon filter 9 selectively effective towards one or more toxic gases (radon, formaldehyde, etc.) of significant interest for the specific application to which the assembly 1 is intended from time to time.

Downstream of the active carbon filter 9, as seen previously, is therefore arranged at least one electrically polarised fibre filter 10, which may, according to substantially known methods, make the selective locking of pollutants of the solid particles type, having dimensions preferably comprised between 50 μm and 200 μm (and therefore, with lesser dimensions than those at which locking is responsible for perforated plate 8).

It must be noted, moreover, how positively selection of retaining the solid particles of larger dimensions upstream, at perforated plate 8, prevents the hazard that the locked pollutants may be released, due to the possible clogging of the filtering mesh, thus affecting the proper filtering.

Downstream of the activated carbon filter 9, as seen previously, the particle of finer dimensions, up to a few nanometers, can be effectively removed by the air passing through, thanks to the joint action of the grille 4, the filament 6, and the accumulation plates 7.

During the running through along the duct 2, therefore, the air is progressively purified and deprived, besides of the toxic gases, also of the solid polluting particles, of any size and type (be these micro-organisms, dust, particulates, even radioactive), thus achieving complete clean-up of the air thereof.

It is useful noting how in the preferred embodiment of the invention, the perforated plate 8, the active carbon filter 9 and the electrically polarised fibres filter 10 are arranged in series along the duct 2 in the sequence given above (illustrated moreover in FIG. 1), but it is not excluded making the assemblies 1 anyhow included in the scope of protection claimed hereby, in which these components are arranged in the filtering station in a different order, depending on the specific requirements.

Conveniently, as it is also apparent from FIG. 1, the assembly 1 comprises at least one deflection plate 11, kept at a negative electric potential (possibly equal to that to which are kept the filaments 6 and/or the grille 4) and which faces the accumulation plates 7, so as to generate an electric field within the duct 2 for the deviation of pollutants paired with the electrons towards the accumulation plates 7 thereof, facilitating their stable collection (by adhesion) on the latter.

Also the number of deflection plates 11 located within the duct 2, can be selected at will (just like their configuration), without departing from the scope of protection claimed hereby: in FIG. 1 is given a possible embodiment, which envisages a plurality of deflection plates 11, interposed between each pair of adjacent accumulation plates 7.

Conveniently, the assembly 1 according to the invention comprises one or more germicidal lamps 12 which face the accumulation plates 7, to inactivate the pollutants of the micro-organisms type. In particular, according to a possible embodiment, each germicidal lamp 12 is of the type of the low power ultraviolet lamps (without ozone emission), able to radiate in a constant way the accumulation plates 7, on which are collected the micro-organisms paired with the electrons emitted by filament 6.

Advantageously, the assembly 1 may comprise an addressing organ, in turn arranged in proximity of the holes 5 and kept at a different electrical potential (for example equal to the earthing potential), with respect to the electric potential of the filaments 6, to force the electrons emitted by the latter, a predefined trajectory, leading precisely towards the organ thereof, and therefore such as, according to the specific requirements, to intercept the flow of air under the conditions that it is deemed may promote at best pairing with the pollutants.

More particularly, the addressing organ may consist of a coating metal film (for example, made of copper), which can be applied on the grille 4. Alternatively, the organ may consist by a metal mesh, arranged in a parallel way in proximity of the grille 4, and towards which can thus be attracted the electrons emitted by the filaments 6 (and the grille 4 thereof).

Figure 3:
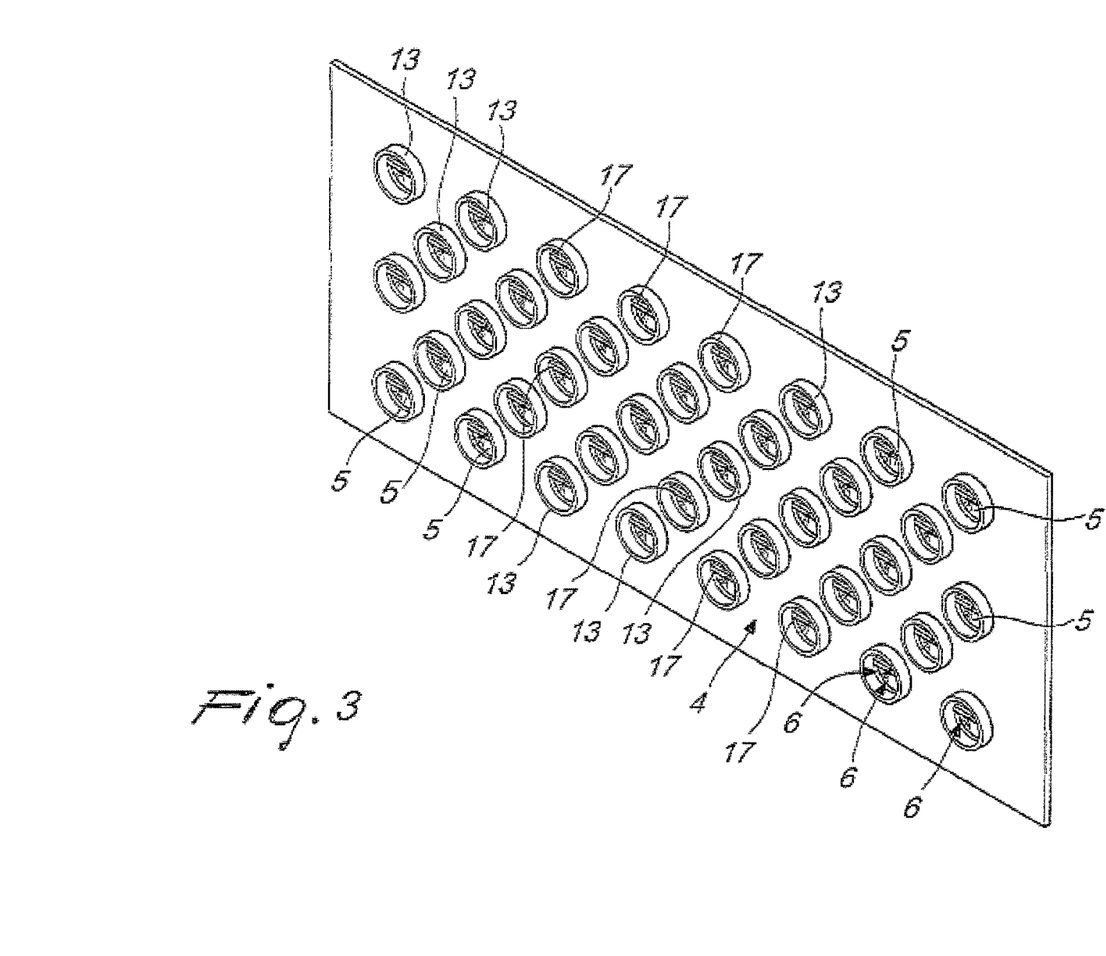
FIG. 3 schematically illustrates the conductive grille, in perspective view, in the second embodiment.

Furthermore, in a third embodiment, illustrated merely by way of example but not limited, in FIG. 3 the addressing organs consist of a coating layer of the cylindrical raised frames top 13, which develop from the edge of the holes 5 with axial extension greater than the length of the filaments 6.

The different proposed embodiments, just like others, possibly adoptable, thus allow varying the emission direction of the electrons, depending on the specific application needs.

Positively, the assembly 1 comprises a conveyor gaseous fluid 14 (for example, a fan), located within the duct 2. The fan can thus suck from the outside, through a plurality of inlets 15, the gaseous fluid carrying the pollutants, which it is desired to treat with the assembly 1 and to determine the forced conveyance thereof towards an outlet 16, emitting it to the outside, after having removed the pollutants and having restored the desired electrical charge.

In the non-limiting application of the preferred embodiment of the invention, the filtering station comprises a plurality of perforated plates 8, arranged so as to face to respective inlets 15; in addition, to each perforated plate 8, on the opposite side with respect to the inlets 15, respective active carbon filters 9 are fixed.

These active carbon filters 9 can usefully have corresponding catalytic activators, for an optimal adsorption of pollutants of the toxic gases type (avoiding the hazard that only the adsorption by molecular attraction of the active carbon cavities cannot remove at best the toxic gases).

In addition, advantageously, with further reference to the preferred embodiment, but not exclusive, on each active carbon filter 9, from the opposite side with respect to the perforated plates 8, is applied a respective filter 10 with electrically polarized fibres, substantially consisting of a cloth composed of these fibres.

The filtering method for air and gaseous fluids generally consists, in a first step a., in intercepting a gaseous fluid, carrying pollutants of various types with a flow of electrons, emitted both by a conductive grille 4, arranged along the duct 2 and having at least one hole 5, and by at least one conductive filament 6 which faces and is proximate to the hole 5.

Both the grille 4 and the filament 6 are kept at a negative electric potential in order to obtain the pairing, for example, by electrostatic attraction, of the electrons (for the emission of which filament 6 constitutes a privileged source) with pollutants of the solid particles and micro-organisms type, having sizes preferably between 10 nm and 50 μm.

Subsequently, the pollutants paired with the electrons can be collected in a step b., on an accumulation plate 7, kept for this purpose to a positive electric potential and arranged along the duct 2 downstream of the grille 4.

Furthermore, the method according to the invention envisages in a step c., to restore the electric charge of the gaseous fluid (be it air or other), by means of an emission source of ions A, arranged along the duct 2 downstream of the grille 4 and the accumulation plate 7.

First (as in the preferred embodiment), or after steps a., b., c. listed above, or even at an intermediate time among these, the method according to the invention envisages also in a step d., to remove from the gaseous fluid (be it air, according to the preferred embodiment, or other) pollutants of the toxic gases and solid particles type, having dimensions preferably greater than 50 μm, at at least one filtering station, arranged along a duct 2, that can be crossed by the gaseous fluid thereof.

More particularly, as seen previously, the filtering station, which allows execution of step d., of removal of the method according to the invention, comprises (in any sequence, but preferably arranged in series along the duct 2 in the order proposed hereby): at least one perforated plate 8, which comprises in its turn at least one opening with dimensions preferably comprised between 150 μm and 250 μm, at least one active carbon filter 9 for the adsorption of pollutants of the toxic gases type, and at least one electrically polarised fibre filter 10 for the selective locking of pollutants of the solid particles type having dimensions preferably between 50 μm and 200 μm.

Perforated plate 8 allows free passage of the gaseous fluid, but selectively locks the pollutants, of the solid particles type with larger dimensions than those of the opening mentioned above.

It is therefore evident how the assembly 1 according to the invention (and the method according to the invention) allow carrying out, in a suitable sequence, a plurality of filtering activities, in such a way as to ensure an effective and optimal removal of different types of pollutants (particulate of any dimension, micro-organisms, toxic gases, by rebalancing at the same time the content of negative ions), carried by the treated air, ensuring well-being and health conditions to individuals who work in environments in which it is installed.

In fact, the first pre-filtering stage allows in the first place to remove from the air (that runs through the duct 2, forced by the fan) the solid particles of greater dimensions; subsequently, after eliminating even the toxic gases thanks to the active carbon filter 9, the electrically polarised fibre filter 10 locks selectively the pollutants on the solid particle type with dimensions preferably between 50 μm and 200 μm.

Subsequently, the air crosses the holes 5 of the grille 4, thus flowing over the filaments 6: the solid particles of finer dimensions (be these particulates, micro-organisms, or other) can thus be paired with the electrons emitted by the filaments 6 and from the grille 4, to be thus directed (with the contribution of the deflection plates 11) towards the accumulation plates 7.

Assembly 1 can therefore perform different filtering treatments on solid particles (of whatever type should they be), each of which for pollutants of progressively decreasing dimensions, to achieve the total removal of these particles (or anyhow removal of most part of them); in addition, it is ensured the removal of toxic gases thanks to the active carbon filter 9.

Regarding the pollutants of the micro-organisms type (of whatever type may these be), it is confirmed how these, after being collected on the accumulation plates 7 (and removed by air), may be rendered inactive permanently thanks to germicidal lamps 12; ultraviolet sterilisation allows to inactivate micro-organisms by directly acting on their DNA, and precisely because the action of lamps 12 (moreover, arranged in proximity of the accumulation plates 7 to which they are faced) occurs while the micro-organisms have already been removed from the air, it is possible to choose, as seen previously, low power lamps 12, thus limiting consumptions, since the irradiation can take place in a constant way and without time constraints. Downstream of the grille 4 and of the accumulation plates 7, as seen previously, the presence of an emission source of ions A (for example, of the ionising tips type, directed as the flow of air that crosses the duct 2 and facing the outlet 16, or even exiting therefrom), ensures a significant presence of negative ions A in order to rebalance the electric charge. Moreover, since this source acts on air by now unpolluted, it does not become necessary to apply a high voltage power supply, thus excluding a harmful ozone production.

It is specified how the source may emit ions A within the duct 2, downstream of the accumulation plate 7 and/or outside of the duct 2, at the output 16 (as in the example of FIG. 1), depending on the specific application requirements.

It also appears evident how the effective filtering ensured by the assembly 1 (and by the method) according to the invention is achieved in a practical and easy way, without requiring the installation of complex infrastructures and without requiring significant periodic maintenance interventions.

The air emitted into the environment, after the passage through the duct 2, ensures to individuals a pleasant feeling from the olfactory point of view, besides ensuring their physical well-being enduring through time (precisely because it allows breathing clean air), without implying harmful side effects, even (as seen previously) in the absence of maintenance.

Practically, it is found how the assembly and the method according to the invention, fully achieve the intended task, since the use of at least one filtering station, of at least one conductive grille, having at least one hole which faces and is proximate to at least one conductive filament, of at least one accumulation plate located downstream of the grille and of at least one emission source of ions, allows making a filtering assembly of the air, and of the gaseous fluids in general, which results to be effective against different types of pollutants.

For example, experimental tests have shown how through the use of assembly 1 according to the invention (or implementation of the method according to the invention), it is possible to obtain a reduction of the total bacterial load by higher than 90%, a reduction of gaseous chemical pollutants (toxic gases) equivalent to about 15 total air changes every hour, a reduction of the particulate ultra-fine granulometry (dimensions included between 10 nm and 100 nm), besides a reset of the spores concentrations of *aspergillus*, with active source in environment, in only four hours, obtaining a laminar flow of treated air that extends to a distance of up to 6 meters, without causing any discomfort to people.

The invention, thus conceived, is susceptible of numerous modifications and variations, all within the inventive concept; moreover, all the details may be replaced with other technically equivalent elements.

For example, while not excluding the possibility of adopting different configurations, anyhow falling within the protection scope claimed hereby, each filament 6 is preferably made of metallic material and is of the multipolar type.

Furthermore, each filament 6 has a fixed first end rigidly secured to the grille 4 at a diametrical rib 17, which crosses each hole 5, and, on the opposite side, a second free end, spaced from the grille 4 and preferably wedge-shaped, to ensure an optimal emission and dispersion of the electrons.

In the examples of the illustrated embodiments, individual characteristics, given in relation to specific examples, may actually be interchanged with other different characteristics existing in other examples of embodiments.

In practice, the materials used, and the dimensions, may be any, according to the requirements and the state of the technique.

The invention claimed is:

1. A filtering assembly for air and gaseous fluids in general, comprising a duct that can be crossed by a gaseous fluid that carries pollutants of various kinds, wherein said filtering assembly comprises:
   at least one filtering station including
      at least one perforated plate having at least one opening with first dimensions, the at least one perforated plate for free passage of the gaseous fluid and selective blocking of pollutants of the type of solid particles with dimensions greater than the first dimensions,
      at least one activated carbon filter for the adsorption of pollutants of the type of toxic gases, and
      at least one filter with electrically polarized fibers for the selective blocking of pollutants;
   at least one conducting grille, which has at least one hole that faces and is proximate to at least one conducting filament, said at least one grille and said at least one filament being kept at a negative electric potential, for the emission of electrons, which can be paired with pollutants, downstream of said grille there being at least one accumulation plate, which is kept at a positive electric potential, for the stable collection of pollutants paired with the electrons;
   at least one emission source of ions, for restoring the electrical charge of the gaseous fluid that flows over said source.

2. The filtering assembly according to claim 1, wherein said conducting grille has a plurality of holes, each one of said holes facing and being proximate to a respective plurality of conducting filaments, some of said conducting filaments being arranged downstream of each one of said holes, others of said conducting filaments being arranged upstream of each one of said holes.

3. The filtering assembly according to claim 1, further comprising at least one deflection plate, which is kept at a negative electrical potential and faces said at least one accumulation plate, in order to generate an electrical field inside said duct, to divert pollutants paired with the electrons toward said accumulation plate.

4. The filtering assembly according to claim 1, further comprising at least one germicidal lamp, which faces said at least one accumulation plate, for the inactivation of pollutants such as micro-organisms.

5. The filtering assembly according to claim 1, further comprising a conveyor of gaseous fluid, which is arranged inside said duct, for aspirating from outside, through a plurality of inlets, of the gaseous fluid that carries pollutants, and for its forced conveyance toward a delivery outlet, for the outward emission of the gaseous fluid, after the removal of the pollutants and the restoration of the desired electrical charge.

6. The filtering assembly according to claim 5, wherein said filtering station comprises a plurality of said perforated plates, which are arranged so as to face respective of said inlets, respective of said activated carbon filters being fixed to each one of said perforated plates, on the opposite side with respect to said inlets, and being provided with corresponding catalytic activators, for optimum absorption of pollutants of the type of toxic gases.

7. The filtering assembly according to claim 6, wherein a respective said filter with electrically polarized fibers, constituted substantially by a cloth composed of said fibers, is applied on each one of said activated carbon filters, on the opposite side with respect to said perforated plates.

8. The filtering assembly according to claim 1, wherein
   the least one filtering station is for removal of pollutants of the type of toxic gases and solid particles with dimensions greater than 50 µm; and
   the least one conducting grille is for collection of solid particles and micro-organisms having dimensions between 10 nm and 50 µm.

9. The filtering assembly according to claim 8, further wherein
   the first dimensions of the opening of the least one perforated plate are between 150 µm and 250 µm, and
   the least one filter with electrically polarized fibers is for the selective blocking of pollutants of the type of solid particles dimensions preferably between 50 µm and 200 µm.

10. A filtering assembly for air and gaseous fluids in general, comprising a duct that can be crossed by a gaseous fluid that carries pollutants of various kinds, wherein said filtering assembly comprises:
   at least one filtering station;
   at least one conducting grille, which has a plurality of holes, each one of said holes facing and being proximate to a respective plurality of conducting filaments, some of said conducting filaments being arranged downstream of each one of said holes, others of said conducting filaments being arranged upstream of each one of said holes, said at least one grille and said plurality of filaments being kept at a negative electric potential, for the emission of electrons, which can be paired with pollutants, downstream of said grille there being at least one accumulation plate, which is kept at a positive electric potential, for the stable collection of pollutants paired with the electrons;
   at least one emission source of ions, for restoring the electrical charge of the gaseous fluid that flows over said source.

11. The filtering assembly according to claim 10, wherein
   the least one filtering station is for removal of pollutants of the type of toxic gases and solid particles with dimensions greater than 50 µm; and
   the least one conducting grille is for collection of solid particles and micro-organisms having dimensions between 10 nm and 50 µm.

12. The filtering assembly according to claim 10, wherein said filtering station further comprises:
   at least one perforated plate having at least one opening with first dimensions, for free passage of the gaseous fluid and selective blocking of pollutants of the type of solid particles with dimensions greater than the first dimensions;
   at least one activated carbon filter, for the adsorption of pollutants of the type of toxic gases;
   at least one filter with electrically polarized fibers, for the selective blocking of pollutants.

13. The filtering assembly according to claim 12, further wherein
   the first dimensions of the opening of the least one perforated plate are between 150 µm and 250 in, and the least one filter with electrically polarized fibers is for the selective blocking of pollutants of the type of solid particles dimensions preferably between 50 μm and 200 μm.

14. The filtering assembly according to claim 10, further comprising at least one deflection plate, which is kept at a negative electrical potential and faces said at least one accumulation plate, in order to generate an electrical field inside said duct, to divert pollutants paired with the electrons toward said accumulation plate.

15. The filtering assembly according to claim 10, further comprising at least one germicidal lamp, which faces said at least one accumulation plate, for the inactivation of pollutants such as micro-organisms.

16. The filtering assembly according to claim 10, further comprising a conveyor of gaseous fluid, which is arranged inside said duct, for aspirating from outside, through a plurality of inlets, of the gaseous fluid that carries pollutants, and for its forced conveyance toward a delivery outlet, for the outward emission of the gaseous fluid, after the removal of pollutants and the restoration of the desired electrical charge.

17. The filtering assembly according to claim 16, wherein said filtering station comprises a plurality of said perforated plates, which are arranged so as to face respective of said inlets, respective of said activated carbon filters being fixed to each one of said perforated plates, on the opposite side with respect to said inlets, and being provided with corresponding catalytic activators, for optimum absorption of pollutants of the type of toxic gases.

18. The filtering assembly according to claim 17, wherein a respective said filter with electrically polarized fibers, constituted substantially by a cloth composed of said fibers, is applied on each one of said activated carbon filters, on the opposite side with respect to said perforated plates.

19. A filtering assembly for air and gaseous fluids in general, comprising a duct that can be crossed by a gaseous fluid that carries pollutants of various kinds, wherein said filtering assembly comprises:
a conveyor of gaseous fluid, which is arranged inside said duct, for aspirating from outside, through a plurality of inlets, of the gaseous fluid that carries pollutants, and for its forced conveyance toward a delivery outlet, for the outward emission of the gaseous fluid, after the removal of pollutants and the restoration of the desired electrical charge;
at least one filtering station comprising a plurality of said perforated plates, which are arranged so as to face respective of said inlets, respective of activated carbon filters being fixed to each one of said perforated plates, on the opposite side with respect to said inlets, and being provided with corresponding catalytic activators, for optimum absorption of pollutants of the type of toxic gases;
at least one conducting grille, which has at least one hole that faces and is proximate to at least one conducting filament, said at least one grille and said at least one filament being kept at a negative electric potential, for the emission of electrons, which can be paired with pollutants, downstream of said grille there being at least one accumulation plate, which is kept at a positive electric potential, for the stable collection of the pollutants paired with the electrons;
at least one emission source of ions, for restoring the electrical charge of the gaseous fluid that flows over said source.

20. The filtering assembly according to claim 19, wherein the least one filtering station is for removal of pollutants of the type of toxic gases and solid particles with dimensions greater than 50 μm; and
the least one conducting grille is for collection of solid particles and micro-organisms having dimensions between 10 nm and 50 μm.

21. The filtering assembly according to claim 19, wherein said perforated plates each have at least one opening with first dimensions, for free passage of the gaseous fluid and selective blocking of pollutants of the type of solid particles with dimensions greater than the first dimensions, and
said filtering station further comprises at least one filter with electrically polarized fibers, for the selective blocking of pollutants.

22. The filtering assembly according to claim 21, further wherein
the first dimensions of the opening of the perforated plates are between 150 μml and 250 μm, and
the least one filter with electrically polarized fibers is for the selective blocking of pollutants of the type of solid particles dimensions preferably between 50 μm and 200 μm.

23. The filtering assembly according to claim 19, wherein said conducting grille has a plurality of holes, each one of said holes facing and being proximate to a respective plurality of conducting filaments, some of said conducting filaments being arranged downstream of each one of said holes, others of said conducting filaments being arranged upstream of each one of said holes.

24. The filtering assembly according to claim 21, wherein said conducting grille has a plurality of holes, each one of said holes facing and being proximate to a respective plurality of conducting filaments, some of said conducting filaments being arranged downstream of each one of said holes, others of said conducting filaments being arranged upstream of each one of said holes.

25. The filtering assembly according to claim 19, further comprising at least one deflection plate, which is kept at a negative electrical potential and faces said at least one accumulation plate, in order to generate an electrical field inside said duct, to divert the pollutants paired with the electrons toward said accumulation plate.

26. The filtering assembly according to claim 19, further comprising at least one germicidal lamp, which faces said at least one accumulation plate, for the inactivation of pollutants such as micro-organisms.

27. The filtering assembly according to claim 19, wherein a respective said filter with electrically polarized fibers, constituted substantially by a cloth composed of said fibers, is applied on each one of said activated carbon filters, on the opposite side with respect to said perforated plates.

* * * * *